(12) United States Patent
Hastings et al.

(10) Patent No.: US 6,759,512 B1
(45) Date of Patent: Jul. 6, 2004

(54) HUMAN NEURONAL ATTACHMENT FACTOR-1

(75) Inventors: Gregg Hastings, Newberry Park, CA (US); Patrick J. Dillon, Gaithersburg, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/170,042

(22) Filed: Oct. 13, 1998

Related U.S. Application Data

(62) Division of application No. 08/799,173, filed on Feb. 12, 1997, now Pat. No. 5,871,969.
(60) Provisional application No. 60/011,519, filed on Feb. 12, 1996.

(51) Int. Cl.[7] .................... C07K 14/435; C07K 14/00; C07K 7/08

(52) U.S. Cl. ................... 530/350; 530/324; 530/325; 530/326; 530/327; 424/185.1

(58) Field of Search ................... 530/350, 324, 530/325, 326, 327, 328, 329; 424/185.1; 514/2, 12

(56) References Cited

U.S. PATENT DOCUMENTS 5,279,966 A  *  1/1994  Jessell et al. ............ 435/320.1

OTHER PUBLICATIONS

Skolnick et al. Trends in Biotech. 18(1) 34–39, 2000.*
Rudinger, In "Peptide Hormones" (ed. J.A. Parsons) University Park Press, Baltimore, pp. 1–7, 1976.*
Hillier, L., et al., GenBank Acces. No. T81066, Mar. 15, 1995.

* cited by examiner

*Primary Examiner*—Gary Kunz
*Assistant Examiner*—Robert C. Hayes
(74) *Attorney, Agent, or Firm*—Human Genome Sciences, Inc.

(57) ABSTRACT

A human F-spondin-like protein and DNA (RNA) encoding such protein and a procedure for producing such protein by recombinant techniques is disclosed. Also disclosed are methods for utilizing such polypeptide for treating spinal cord injuries and damage to peripheral nerves by promoting neural-cell adhesion and neurite extension, inhibiting tumor metastases and tumor angiogenesis, and stimulating wound repair. Antagonists are also disclosed which may be utilized to prevent malaria. Diagnostic assays for identifying mutations in nucleic acid sequence encoding a polypeptide of the present invention and for detecting altered levels of the polypeptide of the present invention for detecting diseases, for example, cancer, are also disclosed.

14 Claims, 4 Drawing Sheets

| | | |
|---|---|---|
| 1 | CGCTGCTCCTGCCGGGTGATGGAAAACCCCAGCCCGGCCGCCGCCCTGGGCAAGGCCCTC | 60 |
| 1 |                      M  E  N  P  S  P  A  A  A  L  G  K  A  L | 20 |
| 61 | TGCGCTCTCCTCCTGGCCACTCTCGGCGCCGCCGGCCAGCCTCTTGGGGGAGAGTCCATC | 120 |
| 21 | C  A  L  L  L  A  T  L  G  A  A  G  Q  P  L  G  G  E  S  I | 40 |
| 121 | TGTTCCGCCAGAGCCCTGGCCAAATACAGCATCACCTTCACGGGCAAGTGGAGCCAGACG | 180 |
| 41 | C  S  A  R  A  L  A  K  Y  S  I  T  F  T  G  K  W  S  Q  T | 60 |
| 181 | GCCTTCCCCAAGCAGTACCCCCTGTTCCGCCCCCCTGCGCAGTGGTCTTCGCTGCTGGGG | 240 |
| 61 | A  F  P  K  Q  Y  P  L  F  R  P  P  A  Q  W  S  S  L  L  G | 80 |
| 241 | GCCGCGCATAGCTCCGACTACAGCATGTGGAGGAAGAACCAGTACGTCAGTAACGGGCTG | 300 |
| 81 | A  A  H  S  S  D  Y  S  M  W  R  K  N  Q  Y  V  S  N  G  L | 100 |
| 301 | CGCGACTTTGCGGAGCGCGGCGAGGCCTGGGCGCTGATGAAGGAGATCGAGGCGGCGGGG | 360 |
| 101 | R  D  F  A  E  R  G  E  A  W  A  L  M  K  E  I  E  A  A  G | 120 |
| 361 | GAGGCGCTGCAGAGCGTGCACGCGGTGTTTTCGGCGCCCGCCGTCCCCAGCGGCACCGGG | 420 |
| 121 | E  A  L  Q  S  V  H  A  V  F  S  A  P  A  V  P  S  G  T  G | 140 |
| 421 | CAGACGTCGGCGGAGCTGGAGGTGCAGCGCAGGCACTCGCTGGTCTCGTTTGTGGTGCGC | 480 |
| 141 | Q  T  S  A  E  L  E  V  Q  R  R  H  S  L  V  S  F  V  V  R | 160 |
| 481 | ATCGTGCCCAGCCCCGACTGGTTCGTGGGCGTGGACAGCCTGGACCTGTGCGACGGGGAC | 540 |
| 161 | I  V  P  S  P  D  W  F  V  G  V  D  S  L  D  L  C  D  G  D | 180 |
| 541 | CGTTGGCGGGAACAGGCGGCGCTGGACCTGTACCCCTACGACGCCGGGACGGACAGCGGC | 600 |
| 181 | R  W  R  E  Q  A  A  L  D  L  Y  P  Y  D  A  G  T  D  S  G | 200 |
| 601 | TTCACCTTCTCCTCCCCCAACTTCGCCACCATCCCGCAGGACACGGTGACCGAGATAACG | 660 |
| 201 | F  T  F  S  S  P  N  F  A  T  I  P  Q  D  T  V  T  E  I  T | 220 |
| 661 | TCCTCCTCTCCCAGCCACCCGGCCAACTCCTTCTACTACCCGCGGCTGAAGGCCCTGCCT | 720 |
| 221 | S  S  S  P  S  H  P  A  N  S  F  Y  Y  P  R  L  K  A  L  P | 240 |
| 721 | CCCATCGCCAGGGTGACACTGGTGCGGCTGCGACAGAGCCCCAGGGCCTTCATCCCTCCC | 780 |
| 241 | P  I  A  R  V  T  L  V  R  L  R  Q  S  P  R  A  F  I  P  P | 260 |
| 781 | GCCCCAGTCCTGCCCAGCAGGGACAATGAGATTGTAGACAGCGCCTCAGTTCCAGAAACG | 840 |
| 261 | A  P  V  L  P  S  R  D  N  E  I  V  D  S  A  S  V  P  E  T | 280 |
| 841 | CCGCTGGACTGCGAGGTCTCCCTGTGGTCGTCCTGGGGACTGTGCGGAGGCCACTGTGGG | 900 |
| 281 | P  L  D  C  E  V  S  L  W  S  S  W  G  L  C  G  G  H  C  G | 300 |
| 901 | AGGCTCGGGACCAAGAGCAGGACTCGCTACGTCCGGGTCCAGCCCGCCAACAACGGGAGC | 960 |
| 301 | R  L  G  T  K  S  R  T  R  Y  V  R  V  Q  P  A  N  N  G  S | 320 |
| 961 | CCCTGCCCCGAGCTCGAAGAAGAGGCTGAGTGCGTCCCTGATAACTGCGTCTAAGACCAG | 1020 |
| 321 | P  C  P  E  L  E  E  E  A  E  C  V  P  D  N  C  V  * | 340 |
| 1021 | AGCCCCGCAGCCCCTGGGGCCCCCCGGAGCCATGGGGTGTCGGGGGCTCCTGTGCAGGCT | 1080 |
| 1081 | CATGCTGCAGGCGGCCGAGGGCACA | 1105 |

FIG.1

```
rFSP    151  PTGTGCVILKASIVQKRIIYFQDEGSLTKKLCEQDPTLDGVTDRPILD..  198
                             ..:.|.| ||.   |...|: :
NAF-1     1  ................MENPSPAAALGKALCALLLATLGAAGQPLGGES   33 rFSP    199  .CCACGTAKYRLTFYGNWSEKTHPKDYP...RRANHWSAIIGGSHSKNYVL  245
             |:|  :  |||..:|| |.||:.. ||:||  ].:.:||.::|:.||.:| :
NAF-1    34  ICSARALAKYSITFTGKWSQTAFPKQYPLFRPPAQWSSLLGAAHSSDYSM   83 rFSP    246  WEYGGYASEGVKQVAELGSPVKMEEEIRQQSDEVLTVIKAKAQWPSWQPV   295
             |  ..|.|:|::..|| |.: : .||  ..::: .|  .| :.. ...
NAF-1    84  WRKNQYVSNGLRDFAERGEAWALMKEIEAAGEALQSV...HAVFSAPAVP  130 rFSP    296  NVRAAPSAEFSVDRTRHLMSFLTMMGPSPDWNVGLSAEDLCTKECGWVQK  345
             ..  :...|||:.|:|  :  |:||:...:|||| ||:..  |||. :  : |
NAF-1   131  SGTGQTSAELEVQRRHSLVSFVVRIVPSPDWFVGVDSLDLCDGDRWREQA  180 rFSP    346  VVQDLIPWDAGTDSGVTYESPNKPTIPQEKIRPLT..SLDHPQSPFYDPE  393
             .: ||.|:||||||.|:.||| :|||||:..:|  | .||...|| |
NAF-1   181  AL.DLYPYDAGTDSGFTFSSPNFATIPQDTVTEITSSSPSHPANSFYYPR  229 rFSP    394  GGSITQVARVVIERIARKGEQCNIVPDNVDDIVADLAPEEKDEDDTPETC  443
             .:...:|||.: |:  |.:...  |.|. |  .:  .:  .,:|| .|
NAF-1   230  LKALPPIARVTLVRL.RQSPRAFIPPAPVLPSRDNEIVDSASVPETPLDC  278 rFSP    444  IYSNWSPWSACSSSTCEKGKRMRQRMLKAQ.LDLSVPCPDTQDFQPCMGP  492
               | ||.| |::  .. |.:  | |  ::.|   :  :  |||: ::  ..|:..
NAF-1   279  EVSLWSSWGLCGGHCGRLGTKSRTRYVRVQPANNGSPCPELEEEAECVPD  328 rFSP    493  GCSDEDGSTCTMSEWITWSPCSVSCGMGMRSRERYVKQFPEDGSVCMLPT  542
             .|
NAF-1   329  NCV...............................................  331
```

FIG.2

```
        C L V S E W S E W S D C S - - T C G K - G M R S R T R M V K    Majority
                        10              20              30
    1   C E V S L W S S W G L C G - G H C G R L G T K S R T R Y V R    FLP-TSR
    1   C I Y S N W S P W S A C S S T C E K - G K R M R Q R M L K    FSP-TSR-1
    1   C T M S E W I T W S P C S V - S C G M - G M R S R E R Y V K    FSP-TSR-2
    1   C L V T E W G E W D D C S A - T C G M - G M K K R H R M V K    FSP-TSR-3
    1   C L L S P W S E W S D C S V - T C G K - G M R T R Q R M L K    FSP-TSR-4
    1   C E L S E W S Q W S E C N - K S C G K - G H M I R T R T I Q    FSP-TSP-5
    1   C R M R P W T A W S E C T - K L C G G - G I Q E R Y M T V K    FSP-TSP-6

M S P A - D G S P C P - D T E E A E K C M V P E - C            Majority
                        40              50
    30  V Q P A N N G S P C P - E L E E E A E C V - P D N C            FLP-TSR
    30  A Q L D - L S V P C P - D T Q D F Q P C M G P G - C            FSP-TSR-1
    29  Q F P E - D G S V C M L P T E E T E K C T V N E E C            FSP-TSR-2
    29  M S P A - D G S M C K A E I S Q A E K C M M P E - C            FSP-TSR-3
    29  - S L A - E L G D C N E D L E Q A E K C M L P E - C            FSP-TSR-4
    29  M E P Q F G G A P C P - E T V Q R K K C R - A R K C            FSP-TSR-5
    29  K R F K S S Q F T S C K D K K E I R A C N V H P - C            FSP-TSR-6
```

FIG.3

HUMAN NEURONAL ATTACHMENT FACTOR-1

This application is a division application Ser. No. 08/799,173, filed on Feb. 12, 1997, now U.S. Pat. No. 5,871,969 which claims benefit of U.S. Provisional Application Serial No. 60/011,519 filed Feb. 12, 1996.

This invention relates to newly identified polynucleotides, polypeptides encoded by such polynucleotides, the use of such polynucleotides and polypeptides, as well as the production of such polynucleotides and polypeptides. More particularly, the polypeptide of the present invention has been putatively identified as a human neuronal attachment factor-1, sometimes hereinafter referred to as "NAF-1". The invention also relates to inhibiting the action of such polypeptides.

BACKGROUND OF THE INVENTION

F-spondin (FSP) is a gene that is predominantly expressed during the early development of the vertebrate nervous system. The main function is thought to be in neural cell pattern formation and axonal growth. It was found in a subtractive hybridization screen designed to isolate floor-plate specific genes. The floor-plate provides diffusible signals that act on the neurons that extend from the developing spinal cord. These signals can lead to chemoattraction and fasciculation of commissural axons in the ventral midline. F-spondin mRNA is expressed at high levels in the developing neural tube at the ventral midline even before cell differentiation markers can detect the floor-plate. F-spondin is not detectable in other regions of the spinal cord until later in embryonic life. There is also transient F-spondin expression early in peripheral nerve development which diminishes to undetectable levels following birth. The adult central nervous system contains F-spondin while the peripheral nerve (sciatic nerve) does not. Outside the adult nervous system, organs such as the lung and kidney also express F-spondin. The protein is 807 anmino acids and codes for a predicted 90 kD polypeptide. The apparent size is approximately 116 kD by SDS-PAGE which indicates post-translational modifications such as glycosylation. There are six domains homologous to the thrombospondin (TSP) type 1 repeats (TSR) which have been shown to control cell adhesion. The protein has been expressed in COS cells and purified as a myc-tag fusion protein. This protein was active in promoting neurite extension and adhesion of embryonic dorsal root ganglion and dorsal spinal cords respectively. It was not chemotropic for embryonic dorsal spinal cord neurons. (Klar, A. et al., Cell, 69:95–110 (1992)).

The C-terminal half of F-spondin contains 6 repeats identified in thrombospondin and other proteins implicated in cell adhesion. Thrombospondin is a 450,000-dalton glyco-protein secreted by platelets in response to such physiological activators as thrombin and collagen (Lawler, J., Blood, 67:1197–1209 (1986)). TSP comprises 3% of the total platelet protein and 25% of the total platelet-secreted proteins (Tuszynslci, G. P., et al., J. Biol. Chem., 260:12240–12245 (1985)). Although the precise biological role of TSP has yet to be fully established, it is generally accepted that TSP plays a major role in cell adhesion and cell-cell interactions. It should be pointed out that the C-terminal repeats present in thrombospondin may have different biological activities.

TSP was found to promote the cell-substratum adhesion of a variety of cells, including platelets, melanoma cells, smooth muscle cells, endothelial cells, fibroblasts and epithelial cells (Tuszynski, G. P., et al., Science (Washington, D.C.), 236:1570–1573 (1983)).

Thrombospondin has been postulated to play a role in malarial infection induced by only one strain of malaria, *plasmodium falciparum*. During malarial infection, TSP promotes adhesion of parasitized red cells to endothelial cells (Roberts, D. D., et al., Nature (Lond.), 318:64–66 (1984)) and during tumor cell metastases TSP promotes adhesion of mouse sarcoma cells to the vascular bed and expression of the malignant phenotype of small cell carcinoma (Castle, V. J., J. Clin. Invest., 87:1883–1883 (1991)).

Properdin is a complement-binding protein which also contains the 6 terminal repeats found in thrombospondin. UNC-5, a *C. elegans* gene that bears two terminal repeats, appears to guide the axonal extension of the sub-set of neurons. These proteins, which contain at least one member of the six terminal repeats, form a family of proteins which have related functions.

The gene and polypeptide encoded thereby of the present invention has been putatively identified as an Neuronal Attachment Factor-1 protein as a result of amino acid sequence homology to rat F-spondin.

SUMMARY OF THE INVENTION

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, cDNAs, genomic DNAs as well as analogs and biologically active and diagnostically or therapeutically useful fragments thereof.

In accordance with another aspect of the present invention there is provided an isolated nucleic acid molecule encoding a mature polypeptide expressed by the human cDNA contained in ATCC Deposit No. 97343.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the presentcinvention, there is provided a process for utilizing such polypeptide, or polynucleotide encoding such polypeptide for therapeutic purposes, for example, to treat spinal cord injuries or damage to peripheral nerves by promoting neural cell adhesion and neurite extension, to inhibit tumor cell metastases, inhibit endothelial cell proliferation, adhesion and motility, to decrease tumor neovascularization, to be angiostatic for tumor cells and to promote wound healing.

In accordance with yet a further aspect of the present invention, there are provided antibodies against such polypeptides, which would bind to and neutralize NAF-1 to inhibit its putative cell adhesion properties to restrict metastases, particularly tumor metastases.

In accordance with another aspect of the present invention, there are provided NAF-1 agonists which mimic NAF-1 and binds to the NAF-1 receptors.

In accordance with yet another aspect of the present invention, there are provided antagonists to such polypeptides, which may be used to inhibit the action of such polypeptides, for example, in the treatment of malarial infection caused by *Plasmodium falciparum*.

In accordance with yet a further aspect of the present invention, there is also provided nucleic acid probes comprising nucleic acid molecules of sufficient length to hybridize to a nucleic acid sequence of the present invention.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIG. 1 is an illustration of the cDNA (SEQ ID NO:1) and corresponding amino acid sequence (SEQ ID NO:2) of the polypeptide of the present invention. Sequencing was performed using a 373 automated DNA sequencer (Applied Biosystems, Inc.). The putative leader sequence region is underlined.

FIG. 2 is an amino acid sequence comparison between the polypeptide of the present invention (bottom line) (SEQ ID NO:2) and rat F-spondin (rFSP) (top line) (SEQ ID NO:7).

FIG. 3 is an amino acid sequence comparison between the cell adhesion sequence of NAF-1 (FLP-TSR; SEQ ID NO:19) and the six cell adhesion sequences of rat F-spondin (FSR-TSR-1, -2, -3, -4, -5, and -6; SEQ ID NOS:8–13, respectively). Also shown is a TSR consensus sequences shown in the sequence listing as SEQ ID NO:14.

DETAILED DESCRIPTION

Figure 4:
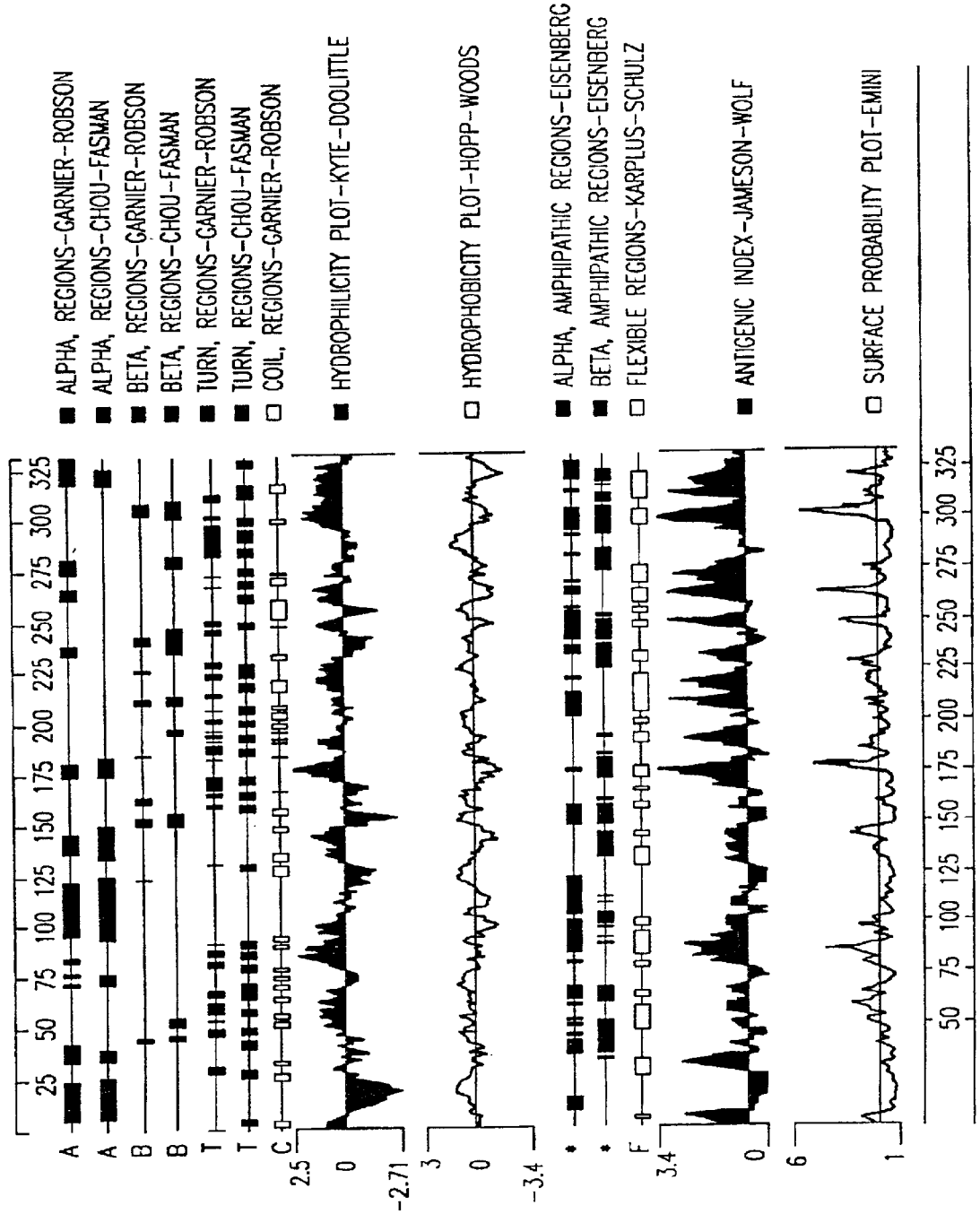
FIG. 4 shows an analysis of the NAF-1 amino acid sequence (SEQ ID NO:2). Alpha, beta, turn and coil regions; hydrophilicity and hydrophoicity; amphipathic regions; flexible regions; antigenic index and surface probability are shown. In the "Antigenic Index-Jameson-Wolf" graph, the positive peaks indicate locations of the highly antigenic regions of the NAF-1 protein, i.e., regions from which epitope-bearing peptides of the invention can be obtained.

In accordance with an aspect of the present invention, there is provided an isolated nucleic acid (polynucleotide) which encodes for the mature polypeptide having the deduced amino acid sequence of FIG. 1 (SEQ ID NO:2).

The polynucleotide of this invention was discovered in a cDNA library derived from human epithelioid sarcoma. It is structurally related to the rat F-spondin family. It contains an open reading frame encoding a protein of 331 amino acid residues. The protein exhibits the highest degree of homology to rat F-spondin with 33.1% identity and 52.9% similarity over the entire amino acid stretch. The gene of the present invention shows the greatest homology at the nucleotide level to the rat F-spondin gene with 66% similarity and 66% identity. It is also important that the polypeptide of the present invention contains the conserved motif, WSXW, which is a potential binding sequence for polypeptides in this family.

Northern blot analysis of the protein of the present invention showed a broad band at 1.6–1.9 kb in liver and lower level expression in kidney, lung, heart and placenta. Brain expression was barely detectable. Two libraries which were constructed from tissues induced to undergo apoptosis, apoptotic t-cells (HTG) and TNF induced amniotic cells (HAU), had one clone in each. By extrapolation, NAF-1 was represented at least 50 times more frequently in apoptotic t-cells expressed sequence tags than all normal and activated t-cell libraries. In the TNF induced amniotic cells library, NAF-1 was detected 1 out of 2,414 expressed sequence tags versus 0 out of 3,595 expressed sequence tags for the non-TNF treated amniotic cell library.

The NAF-1 cDNA contains an open reading frame encoding a polypeptide of 35.8 kD. Amino acids 1–23 and 1–26 encode putative signal peptides. Accordingly, there are two species of predicted mature NAF-1 polypeptides one having 311 and the other 314 amino acids. NAF-1 also contains a putative N-linked glycosylation site at position 303. The homology of NAF-1 to FSP covers amino acids 199–495 of the latter protein. Thus, NAF-1 does not appear to be the human counterpart of the rat FSP. NAF-1 contains only one TSR which begins at amino acid 278. This region is much more homologous to FSP type 1 repeats than to those of TSP, 38% versus 20%, respectively. The homology between the NAF-1 TSR and the six FSP type-1 repeats is shown in FIG. 3. The amino terminal 277 amino acid of NAF-1 share homology to FSP but show no resemblance to any other known proteins.

In accordance with another aspect of the present invention there are provided isolated polynucleotides encoding a mature polypeptide expressed by the human cDNA contained in ATCC Deposit No. 97343, deposited with the American Type Culture Collection, 12301 Park Lawn Drive; Rockville, Md. 20852, USA, on Nov. 20, 1995. The deposited material is a pBluescript SK (−) (Stratagene, La. Jolla, Calif.) plasmid that contains the full-length NAF-1 cDNA. The NAF-1 cDNA has been cloned into the EcoRI, XhoI site.

The deposit has been made under the terms of the Budapest Treaty on the International Recognition of the Deposit of Micro-organisms for purposes of Patent Procedure. The strain will be irrevocably and without restriction or condition released to the public upon the issuance of a patent. The deposit is provided merely as convenience to those of skill in the art and are not an admission that a deposit is required under 35 U.S.C. §112. The sequence of the polynucleotide contained in the deposited material, as well as the amino acid sequence of the polypeptides encoded thereby, are controlling in the event of any conflict with any description of sequences herein. A license may be required to make, use or sell the deposited material, and no such license is hereby granted.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or may be a different coding sequence which coding sequence, as a result of the redundancy or degeneracy of the genetic code, encodes the same mature polypeptide as the DNA of FIG. 1 (SEQ ID NO:1).

The polynucleotide which encodes for the mature polypeptide of FIG. 1 (SEQ ID NO:2) may include, but is not limited to: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2). The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) as well as variants of such polynucleotides which variants encode for a fragment, derivative or analog of the polypeptide of FIG. 1 (SEQ ID NO:2). Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

Most highly preferred are nucleic acid molecules encoding the mature protein having the amino acid sequence shown in SEQ ID NO:2 as residues 24–331 or 27–331, or the mature NAF-1 amino acid sequence encoded by the deposited cDNA clone.

Also highly preferred are nucleic acid molecules encoding the TSR domain of the protein having the amino acid sequence shown in SEQ ID NO:8 or the TSR domain of the NAF-1 amino acid sequence encoded by the deposited cDNA clone.

Thus, one aspect of the invention provides an isolated nucleic acid molecule comprising a polynucleotide having a nucleotide sequence selected from the group consisting of: (a) a nucleotide sequence encoding a full-length NAF-1 polypeptide having the complete amino acid sequence in SEQ ID NO:2, or the complete amino acid sequence encoded by the cDNA clone contained in the ATCC Deposit No. 97343; (b) a nucleotide sequence encoding a full-length NAF-1 polypeptide having the complete amino acid sequence in SEQ ID NO:2 excepting the N-terminal methionine (i.e., positions 2 to 331 of SEQ ID NO:2) or the complete amino acid sequence excepting the N-terminal methionine encoded by the cDNA clone contained in the ATCC Deposit No. 97343; (c) a nucleotide sequence encoding a predicted mature form of the NAF-1 polypeptide having the amino acid sequence at positions 24–331 or 27–331 in SEQ ID NO:2 or as encoded by the cDNA clone contained in the ATCC Deposit No. 97343; (d) a nucleotide sequence encoding a polypeptide comprising the predicted TSR domain of the NAF-1 polypeptide having the amino acid sequence at positions 284–330 in SEQ ID NO:2 or as encoded by the cDNA clone contained in the ATCC Deposit No. 97343; and (e) a nucleotide sequence complementary to any of the nucleotide sequences in (a), (b), (c) or (d) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b), (c), (d) or (e), above, or a polynucleotide which hybridizes under stringent hybridization conditions to a polynucleotide in (a), (b), (c), (d) or (e), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a NAF-1 polypeptide having an amino acid sequence in (a), (b), (c), (d) or (e), above.

The present invention also relates to recombinant vectors, which include the isolated nucleic acid molecules of the present invention, and to host cells containing the recombinant vectors, as well as to methods of making such vectors and host cells and for using them for production of NAF-1 polypeptides or peptides by recombinant techniques.

By a polynucleotide having a nucleotide sequence at least, for example, 95% "identical" to a reference nucleotide sequence encoding a NAF-1 polypeptide is intended that the nucleotide sequence of the polynucleotide is identical to the reference sequence except that the polynucleotide sequence may include up to five point mutations per each 100 nucleotides of the reference nucleotide sequence encoding the NAF-1 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 (SEQ ID NO:1) or to the nucleic acid sequence of the deposited cDNA, irrespective of whether they encode a polypeptide having NAF-1 activity. This is because even where a particular nucleic acid molecule does not encode a polypeptide having NAF-1 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having NAF-1 activity include, inter alia, (1) isolating the NAF-1 gene or allelic variants thereof in a cDNA library; (2) in situ hybridization (e.g., "FISH") to metaphase chromosomal spreads to provide precise chromosomal location of the NAF-1 gene, as described in Verma et al., Human Chromosomes: A Manual of Basic Techniques, Pergamon Press, New York (1988); and Northern Blot analysis for detecting NAF-1 mRNA expression in specific tissues.

Preferred, however, are nucleic acid molecules having sequences at least 90%, 95%, 96%, 97%, 98% or 99% identical to the nucleic acid sequence shown in FIG. 1 (SEQ ID NO:1) or to the nucleic acid sequence of the deposited cDNA which do, in fact, encode a polypeptide having NAF-1 protein activity. By "a polypeptide having NAF-1 activity" is intended polypeptides exhibiting activity similar, but not necessarily identical, to an activity of the mature protein of the invention, as measured in a particular biological assay. For example, the NAF-1 protein of the present invention causes axonal neurite extension and promotes neural cell adhesion. Such activity can be assayed as described in Klar, et al., Cell 69:95–110, incorporated herein by reference.

NAF-1 protein modulates axonal neurite extension and neural cell adhesion in a dose-dependent manner in the above-described assay. Thus, "a polypeptide having NAF-1 protein activity" includes polypeptides that also exhibit any of the same neurite extension and neural cell adhesion promoting activities in the above-described assays in a dose-dependent manner. Although the degree of dose-dependent activity need not be identical to that of the NAF-1 protein, preferably, "a polypeptide having NAF-1 protein activity" will exhibit substantially similar dose-dependence in a given activity as compared to the NAF-1 protein (i.e., the candidate polypeptide will exhibit greater activity or not more than about 25-fold less and, preferably, not more than about tenfold less activity relative to the reference NAF-1 protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) will encode a polypeptide "having NAF-1 protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having NAF-1 protein activity. This is because the skilled artisan is fully aware of amino acid substitutions that are either less likely or not likely to significantly effect protein function (e.g., replacing one aliphatic amino acid with a second aliphatic amino acid), as further described below.

The term "gene" means the segment of DNA involved in producing a polypeptide chain; it includes regions preceding and following the coding region (leader and trailer) as well as intervening sequences (introns) between individual coding segments (exons).

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–1010 of SEQ ID NO:1.

In addition, the invention provides nucleic acid molecules having nucleotide sequences related to extensive portions of SEQ ID NO:1 which have been determined from the following related cDNA clones: HLHCE24R (shown as SEQ ID NO:16); HLHDR83R (shown as SEQ ID NO:17) and HPTSB36R (shown as SEQ ID NO:18).

Further, the invention includes a polynucleotide comprising any portion of at least about 30 nucleotides, preferably at least about 50 nucleotides, of SEQ ID NO:1 from residue 1–650.

More generally, by a fragment of an isolated nucleic acid molecule having the nucleotide sequence of the deposited cDNA or the nucleotide sequence shown in FIG. 1 (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIG. 1 (SEQ ID NO:1). By a fragment at least 20 nt in length, for example, is intended fragments which include 20 or more contiguous bases from the nucleotide sequence of the deposited cDNA or the nucleotide sequence as shown in FIG. 1 (SEQ ID NO:1). Preferred nucleic acid fragments of the present invention include nucleic acid molecules encoding epitope-bearing portions of the NAF-1 polypeptide as identified in FIG. 4 and described in more detail below.

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, at least 50 bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95%, 96%, 97%, 98% or 99% identity between the sequences. The present invention particularly relates to polynucleotides which hybridize under stringent conditions to the hereinabove-described polynucleotides. As herein used, the term "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µm/ml denatured, sheared salmon sperm DNA, followed by washing the filters in 0.1×SSC at about 65° C. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1).

Alternatively, the polynucleotide may have at least 15 bases, preferably at least 30 bases, and more preferably at least 50 bases which hybridize to a polynucleotide of the present invention and which has an identity thereto, as described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95%, 96%, 97%, 98%, or 99% identity to a polynucleotide which encodes the polypeptide of SEQ ID NO:2 and polynucleotides complementary thereto as well as portions thereof, which portions have at least 30 consecutive bases and preferably at least 50 consecutive bases and to polypeptides encoded by such polynucleotides.

The present invention further relates to a polypeptide which has the deduced amino acid sequence of FIG. 1 (SEQ ID NO:2), as well as fragments, analogs and derivatives of such polypeptide.

To improve or alter the characteristics of NAF-1 polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.,* 268:2984–2988 (1993) reported modified KGF proteins that had heparin binding activity even if 3, 8, or 27 amino-terminal amino acid residues were missing. In the present case, since the protein of the invention contains a TSR repeat, deletions of N-terminal amino acids up to the cysteine at position 284 (C284) of SEQ ID NO:2 may retain some biological activity such as the ability to promote cell adhesion, however, additional deletions including C284 would not be expected to retain such biological activities because it is known that this residue in the TSR repeat is required for secondary structure necessary to promote cell adhesion.

However, even if deletion of one or more amino acids from the N-terminus of a protein results in modification or loss of one or more biological functions of the protein, other biological activities may still be retained. Thus, the ability of the shortened protein to induce and/or bind to antibodies which recognize the complete or TSR domain of the protein generally will be retained when less than the majority of the residues of the complete or TSR domain are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the NAF-1 shown in SEQ ID NO:2, up to the C284 residue, and polynucleotides encoding such polypeptides. In particular, the present invention provides polypeptides comprising the amino.

Similarly, many examples of biologically functional C-terminal deletion muteins are known. For instance, interferon gamma shows up to ten times higher activities by deleting 8–10 amino acid residues from the carboxy terminus of the protein (Döbeli et al., *J. Biotechnology* 7:199–216 (1988). However, even if deletion of one or more amino acids from the C-terminus of a protein results in modification of loss of one or more biological ftunctions of the protein, other biological activities may still be retained. Thus, the ability of the shortened protein to induce and/or bind to antibodies which recognize the complete or TSR domain of the protein generally will be retained when less than the majority of the residues of the complete or TSR domain protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the NAF-1 shown in SEQ ID NO:2, up to the C330 residue of SEQ ID NO:2, and polynucleotides encoding such polypeptides. In particular, the present invention provides polypeptides having the amino acid sequence of residues 1-m of the amino acid sequence in SEQ ID NO:2, where m is either 330 or 331, and C330 is the position of the first residue from the C-terminus of the complete NAF-1 polypeptide (shown in SEQ ID NO:2) believed to be required for cell adhesion of the NAF-1 protein.

The invention also provides polypeptides having one or more amino acids deleted from both the amino and the carboxyl termini, which may be described generally as having residues n-m of SEQ ID NO:2, where n and m are integers as described above.

Also included are a nucleotide sequence encoding a polypeptide consisting of a portion of the complete NAF-1 amino acid sequence encoded by the cDNA clone contained in ATCC Deposit No. 97343, where this portion excludes from 1 to about 283 amino acids from the amino terminus of the complete amino acid sequence encoded by the cDNA clone contained in ATCC Deposit No. 97343, or 1 amino acid from the carboxy terminus, or any combination of the above amino terminal and carboxy terminal deletions, of the complete amino acid sequence encoded by the cDNA clone contained in ATCC Deposit No. 97343. Polynucleotides encoding all of the above deletion mutant polypeptide forms also are provided.

In addition to terminal deletion forms of the protein discussed above, it also will be recognized by one of ordinary skill in the art that some amino acid sequences of the NAF-1 polypeptide can be varied without significant effect of the structure or function of the protein. If such differences in sequence are contemplated, it should be remembered that there will be critical areas on the protein which determine activity.

Thus, the invention further includes variations of the NAF-1 polypeptide which show substantial NAF-1 polypeptide activity or which include regions of NAF-1 protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require non-polar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein Thus, the NAF-1 of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the NAF-1 protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol* 2:331–340 (1967); Robbins et al., *Diabetes* 36: 838–845 (1987); Cleland et al., *Crit. Rev. Therapeutic Drug Carrier Systems* 10:307.

FIG. 3 shows the consensus TSR sequence (Sequence ID NO:14). Preferred mutants having increased cell adhesion activity are those with substitutions making the NAF-1 polypeptides more similar to the consensus sequence.

The terms "fragment," "derivative" and "analog" when referring to the polypeptide of FIG. 1 (SEQ ID NO:2), means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The invention further provides an isolated NAF-1 polypeptide comprising an amino acid sequence selected from the group consisting of: (a) the amino acid sequence of the full-length NAF-1 polypeptide having the complete amino acid sequence shown in SEQ ID NO:2 or the complete amino acid sequence excepting the N-terminal methionine encoded by the cDNA clone contained in the ATCC Deposit No. 97343; (b) the amino acid sequence of the full-length NAF-1 polypeptide having the complete amino acid sequence shown in SEQ ID NO:2 excepting the N-terminal methionine (i.e., positions 1–331 of SEQ ID NO:2) or the complete amino acid sequence excepting the N-terminal methionine encoded by the cDNA clone contained in the ATCC Deposit No. 97343; (c) the amino acid sequence of the mature NAF-1 polypeptide having the amino acid sequence of residues 24–331 or 27–331 in SEQ ID NO:2, or the mature NAF-1 amino acid sequence as encoded by the cDNA clone contained in ATCC Deposit No. 97343; and (d) the amino acid sequence of the TSR domain of NAF-1 having the amino acid sequence of residues 284 to 330 of SEQ ID NO:2, or the amino acid sequence of the TSR domain of NAF-1 encoded by the cDNA clone contained in ATCC Deposit No. 97343.

Further polypeptides of the present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited cDNA or to the polypeptide of SEQ ID NO:2, and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a NAF-1 polypeptide is intended that the amino acid sequence of the polypeptide is identical to the reference sequence except that the polypeptide sequence may include up to five amino acid alterations per each 100 amino acids of the reference amino acid of the NAF-1 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited cDNA clone an be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protcon is the immunogen. On the other hand, a region of a protein molecule to which an antibody can bind is defined as an "antigenic epitope." The number of immunogenic epitopes of a protein generally is less than the number of antigenic epitopes. See, for instance, Geysen et aL, *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins," *Science*, 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate NAF-1-specific antibodies include: a polypeptide comprising amino acid residues from about Ak-75 to about Arg-100); a polypeptide comprising amino acid residues from about Lev-168 to about Ala-180); a polypeptide comprising amino acid residues from about Thr-204 to about Tyr 226); and a polypeptide comprising amino acid residues from about Lev-258 to about Ser-281); and a polypeptide comprising amino acid residues from about Gly-291 to about Pro-327). These polypeptide fragments have been determined to bear antigenic epitopes of the NAF-1 protein by the analysis of the Jameson-Wolf antigenic index, as shown in FIG. 4, above.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." *Proc. Natl. Acad. Sci. USA* 82:5131–5135; this "Simultaneous Multiple Peptide Synthesis (SMPS)" process is further described in U.S. Pat. No. 4,631,211 to Houghten et aL (1986).

Epitope-bearing peptides and polypeptides of the invention are used to induce antibodies according to methods well known in the art. See, for instance, Sutcliffe et al., supra; Wilson et al., supra; Chow, M. et al., *Proc. Natl. Acad. Sci. USA* 82:910–914; and Bittle, F. J. et al., *J. Gen. Virol* 66:2347–2354 (1985). Immunogenic epitope-bearing peptides of the invention, i.e., those parts of a protein that elicit an antibody response when the whole protein is the imnmunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmnacia). However, any other plasmid or vector may be used as long as they are replicable and viable in the host.

Promoter regions can be selected from any desired gene using CAT Fat (chloramphenicol transferase) vectors or other vectors with selectable markers. Two appropriate vectors are pKK232-8 and pCM7. Particular named bacterial promoters include lac, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mamnmalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques front a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

NAF-1 may be employed to treat spinal cord injuries or damage to peripheral nerves by increasing spinal cord and sensory neuron attachment and neurite outgrowth.

NAF-1 may also be employed to inhibit tumor cell metastases induced by small cell carcinoma. The NAF-1 gene and gene product of the present invention may also be employed to reduce primary tumor growth, metastatic potential and angiogenesis in human breast carcinoma cells.

The NAF-1 gene and gene product of the present invention may also be employed to promote wound healing due to its ability to promote cell-cell interaction and cell adhesion.

NAF-1 may also be employed to modulate hemostasis.

The polynucleotides and polypeptides of the present invention may be employed as research reagents and materials for discovery of treatments and diagnostics to human disease.

This invention provides a method for identification of the receptor for NAF-1. The gene encoding methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to NAF-1, and a cDNA library created from this RNA is divided into pools and used to transfect COS cells or other cells that are not responsive to NAF-1. Transfected cells which are grown on glass slides are exposed to labeled NAF-1 ligand. NAF-1 can be labeled by a variety of means including iodination or inclusion of a recognition site for a site-specific protein kinase. Following fixation and incubation, the, slides are subjected to autoradiographic analysis. Positive pools are identified and sub-pools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

This invention provides a method of screening compounds to identify those which are agonists to or antagonists to NAF-1. The identification of both type compounds would involve a neurite outgrowth assay. COS cells ($5 \times 10^8$) are transfected with NAF-1/pcDNA-1 (Invitrogen, Inc.) and conditioned medium is collected. NAF$^{myc}$ is affinity purified on a monoclonal anti-myc (9E10) affinity-purified F-spondin$^{myc}$ (20 mg/ml) is absorbed onto nitrocellulose (Lenimon et al., 1989). For controls, parental COS cell-conditioned medium is purified on the same column and used as a substrate on nitrocellulose. The nitrocellulose is then blocked with BSA (10 mg/ml), which provided a further control for background neurite outgrowth. rAT E14 DRG neurons are plated on immobilized protein substrates at a density of $2-10 \times 10^4$ cells per 35 mm tissue culture dish (Nunc) and grown for 14 hr. Cultures are then fixed in 4% paraformaldehyde, permeabilized with 0.1% Triton X-100, and stained using MAb 3A10 (Furley et al., 1990; available from Developmental Studies Hybridoma Bank), which recognizes a neuronal filament-associated protein and serves as a marker for fine neurites. Neuronal cell bodies and neurites are visualized by indirect immunofluorescence on a Zeiss Axioplan microscope. Neurite lengths are measured as the distance from the edge of the soma (sharply defined by 3A10 fluorescence) to the tip of its longest neurite. Neurite lengths are measured if the entire length of the neurite could be unambiguously identified. About 25 neurites are measurable within each protein-coated area (3–4 mm$^2$).

Rat e13 dorsal spinal cord neurons can also be assayed by plating the dissociated cells on immobilized protein substrate at a density of $10^6$ cells per 35 mm tissue culture dish (Nunc). After 1 hr. the cultures are washed twice with PBS and fixed in 4% paraformaldehyde. Cells are counted on a Zeiss Axioplan microscope at 400×magnification. Ten independent counts are taken from each experiment.

An alternative example of identifying agonists and antagonists to the polypeptide of the present invention includes expressing the NAF-1 receptor from a mammalian cell or membrane preparation and incubating that receptor with labeled NAF-1 in the presence of a compound. The ability of a compound to enhance or block the interaction is then quantified. Alternatively, the response of a known second messenger system following interaction of NAF-1 and its receptor would be measured and compared in the presence or absence of the compound. Such second messenger systems include, but are not limited, cAMP guanylate cyclase, ion channels or phosphoinositide hydrolysis.

Potential antagonists include an antibody, or in some cases, an oligopeptide, which binds to the polypeptide. Alternatively, a potential antagonist may be a closely related protein which binds to the receptor sites, however, they are inactive forms of the polypeptide and thereby prevent the action of NAF-1 since receptor sites are occupied.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), thereby preventing transcription and the production of NAF-1. The antisense RNA oligonucleotide hybridizes to the mRNA in vivo and blocks translation of the mRNA molecule into NAF-1 polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of NAF-1.

Potential antagonists include a small molecule which binds to and occupies the catalytic site of the polypeptide thereby making the catalytic site inaccessible to substrate such that normal biological activity is prevented. Examples of small molecules include but are not limited to small peptides or peptide-like molecules.

The antagonists may be employed to treat malarial infection induced by *Plasinodium falciparum*. During malarial infection, the polypeptide of the present invention may promote adhesion of parasitized red cells to endothelial cells and, therefore, antagonists would inhibit this action and prevent malaria. The antagonists may also be employed to treat cancer, for example, in blocking metastasis by inhibiting cell adhesion.

The polypeptides of the present invention or antagonists and agonists may be employed in combination with a suitable pharmaceutical carrier. Such compositions comprise a therapeutically effective amount of the polypeptide or antagonists or agonist, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention or agonists or antagonists may be employed in conjunction with other therapeutic compounds.

The pharmaceutical compositions may be administered in a convenient manner such as by the oral, topical, parenterally, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of admninistration, symptoms, etc.

The NAF-1 polypeptides and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pot III, and b-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus. (CMV) promoter; the respiratory syncytial virus (RSV) promoter; inducible promoters, such as the MMT promoter, the metallothionein promoter; heat shock promoters; the albumin promoter, the ApoAI promoter; human globin promoters; viral thymidine kinase promoters, such as the Herpes Simplex thymidine kinase promoter; retroviral LTRs (including the modified retroviral LTRs hereinabove described); the b-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, y-2, y-AM, PA12, T19-

14X, VT-19-17-H2, yCRE, yCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression of NAF-1, for example, tumor metastases and tumor angiogenesis.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding NAF-1 can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of the polypeptide of the present invention in various tissues since an over-expression of the proteins compared to normal control tissue samples can detect the presence of NAF-1 and conditions related to an overexpression of NAF-1, for example, tumor metastases and angiogenesis. Assays used to detect levels of the polypeptide of the present invention in a sample derived from a host are well-known to those of skill in the art and include radioimmunoassays, competitive-binding assays, Western Blot analysis and preferably an ELISA assay. An ELISA assay initially comprises preparing an antibody specific to the NAF-1 antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attached to any of the polypeptide of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of the polypeptide of the present invention present in a given volume of patient sample when compared against a standard curve.

A competition assay may be employed wherein antibodies specific to the polypeptide of the present invention are attached to a solid support and labeled NAF-1 and a sample derived from the host are passed over the solid support and the amount of label detected attached to the solid support can be correlated to a quantity of the polypeptide of the present invention in the sample.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the sane chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma Technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The above-described antibodies may be employed to isolate or to identify clones expressing the polypeptide or to purify the polypeptide of the present invention by attachment of the antibody to a solid support for isolation and/or purification by affinity chromatography.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described. "Plasmids" are designated by a lower case p preceded and/or followed by capital letters and/or numbers. The starting plasmids herein are either commercially available, publicly available oh an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 mg of plasmid or DNA fragment is used with about 2 units of enzyme in about 20 ml of buffer solution. For the purpose of isolating DNA fragments for plasmid construction, typically 5 to 50 mg of DNA are digested with 20 to 250 units of enzyme in a larger volume. Appropriate buffers and substrate amounts for particular restriction enzymes are specified by the manufacturer. Incubation times of about 1 hour at 37∞ C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 mg of approximately equimolar amounts of the DNA fragments to be ligated. Unless otherwise stated, transformation was performed as described in the method of Graham, F. and Van der Eb, A., Virology, 52:456–457 (1973).

EXAMPLES

Example 1

Bacterial Expression and Purification of NAF-1

The DNA sequence encoding NAF-1, ATCC #97343, is initially amplified using PCR oligonucleotide primers corresponding to the 5' sequences of the processed NAF-1 protein (minus the signal peptide sequence) and the vector sequences 3' to the NAF-1 gene. Additional nucleotides corresponding to NAF-1 are added to the 5' and 3' sequences respectively. The 5' oligonucleotide primer has the sequence 5' GCCATACGGGATCCCAGCCTCTTGGGGGAGAGTCC 3' (SEQ ID NO:3) contains a BamHI restriction enzyme site followed by 21 nucleotides of NAF-1 coding sequence starting from the presumed terminal amino acid of the processed protein codon. The 3' sequence 5' GGCATACGTCTAGATTAGACGCAGTTATCAGGGAC 3' (SEQ ID NO:4) contains complementary sequences to an XbaI site and is followed by 21 nucleotides of NAF-1. The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with BamHI and XbaI. The amplified sequences are ligated into pQE-9 and are inserted in frame with the sequence encoding for the histidine tag and the RBS. The ligation mixture is then used to transform *E. coli* strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized NAF-1 is purified from this solution by chromatography on a Nickel-Chelate column under conditions that allow for tight binding by proteins containing the 6-His tag. NAF-1 is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

Example 2

Cloning and Expression of NAF-1 Using the Baculovirus Expression System

The DNA sequence encoding the full length NAF-1 protein, ATCC #97343, was amplified using PCR oligonucleotide primers corresponding to the 5' and 3' sequences of the gene:

The 5' primer has the sequence 5' GCCATACGGGATCCGCC AT<u>CATG</u>GAAAACCCCAGCCCGGCC 3' (SEQ ID NO:5) and contains a BamHI restriction enzyme site (in bold) followed by 8 nucleotides resembling an efficient signal for the initiation of translation in eukaryotic cells (Kozak, M., J. Mol. Biol., 196:947–950 (1987) which is just behind the first 21 nucleotides of the NAF-1 gene (the initiation codon for translation "ATG" is underlined).

The 3' primer has the sequence 5' GGCATACGTCTAGA <u>TTA</u>GACGCAGTTATCAGGGAC 3' (SEQ ID NO:6) and contains the cleavage site for the restriction endonuclease XbaI and 21 nucleotides complementary to the 3' end of the translated sequence of the NAF-1 gene. The amplified sequences were isolated from a 1% agarose gel using a commercially available kit ("Geneclean," BTO 101 Inc. La Jolla, Calif.). The fragment was then digested with the endonucleases BamHI and XbaI and then purified again on a 1% agarose gel. This fragment is designated F2.

The vector pRG1 (modification of pVL941 vector, discussed below) is used for the expression of the NAF-1 protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa califonica nuclear polyhedrosis virus (AcMNPV) followed by the recognition sites for the restriction endonucleases BamHI and XbaI. The polyadenylation site of the simian virus (SV)40 is used for efficient polyadenylation. For an easy selection of recombinant virus the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid was digested with the restriction enzymes BamHI and XbaI and then dephosphorylated using calf intestinal phosphatase by procedures known in the art. The DNA was then isolated from a 1% agarose gel using the commercially available kit ("Geneclean" BIO 101 Inc., La Jolla, Calif.). This vector DNA is designated V2.

Fragment F2 and the dephosphorylated plasmid V2 were ligated with T4 DNA ligase. *E.coli* XL1 blue cells were then transformed and bacteria identified that contained the plasmid (pBacNAF-1) with the NAF-1 gene using the enzymes BamHI and XbaI. The sequence of the cloned fragment was confirmed by DNA sequencing.

5 mg of the plasmid pBacNAF-1 was co-transfected with 1.0 mg of a commercially available linearized baculovirus ("BaculoGold' baculovirus DNA", Pharmingen, San Diego, Calif.) using the lipofection method (Felgner et al. Proc. Natl. Acad. Sci. USA, 84:7413–7417 (1987)).

1 mg of BaculoGold' virus DNA and 5 mg of the plasmid pBacNAF-1 were mixed in a sterile well of a microtiter plate containing 50 ml of serum free Grace's medium (Life Technologies Inc., Gaithersburg, Md.). Afterwards 10 ml Lipofectin plus 90 ml Grace's medium were added, mixed and incubated for 15 minutes at room temperature. Then the transfection mixture was added drop-wise to the Sf9 insect cells (ATCC CRL 1711) seeded in a 35 mm tissue culture plate with 1 ml if Grace's medium without serum. The plate was rocked back and forth to mix the newly added solution. The plate was then incubated for 5 hours at 27∞ C. After 5 hours the transfection solution was removed from the plate and 1 ml of Grace's insect medium supplemented with 10% fetal calf serum was added. The plate was put back into an incubator and cultivation continued at 27∞ C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution the virus was added to the cells and blue stained plaques were picked with the tip of an Eppendorf pipette. The agar containing the recombinant viruses was then resuspended in an Eppendorf tube containing 200 ml of Grace's medium. The agar was removed by a brief centrifugation and the supernatant containing the recombinant baculovirus was used to infect Sf9 cells seeded in 35 mm dishes. Four days later the supernatants of these culture dishes were harvested and then stored at 4∞ C.

Sf9 cells were grown in Grace's medium supplemented with 10% heat-inactivated FBS. The cells were infected with the recombinant baculovirus V-NAF-1 at a multiplicity of infection (MOI) of 2. Six hours later the medium was removed and replaced with SF900 II medium minus methionine and cysteine (Life Technologies Inc., Gaithersburg). 42 hours later 5 mCi of $^{35}$S-methionine and 5 mCi $^{35}$S cysteine (Amersham) were added. The cells were further incubated for 16 hours before they were harvested by centrifugation and the labelled proteins visualized by SDS-PAGE and autoradiography.

Example 3

Expression of Recombinant NAF-1 in COS Cells

Expression of plasmid, NAF-1 HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, an SV40 intron and polyadenylation site. A DNA fragment encoding the entire NAF-1 precursor and a HA tag fused in frame to its 3' end is cloned into the polylinker region of the vector, placing the recombinant protein expression under control of the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The fusion of HA tag to the NAF-1 protein allows easy detection of the recombinant protein with an antibody that recognizes the HA epitope.

The plasmid construction strategy is described as follows:

The DNA sequence encoding NAF-1; ATCC #97343, is constructed by PCR using two primers as described in the above examples. The 5' primer contains a convenient restriction site followed by a portion of NAF-1 coding sequence starting from the initiation codon; the 3' sequence contains complementary sequences to a convenient restriction site, translation stop codon, HA tag and the last several nucleotides of the NAF-1 coding sequence (not including the stop codon). Therefore, the PCR product contains a convenient 5' and 3' restriction sites, NAF-1 coding sequence followed by HA tag fused in frame, and a translation termination stop codon next to the HA tag. The PCR amplified DNA fragment and the vector, pcDNAI/Amp, are digested and ligated. The ligation mixture is transformed into *E. coli* strain SURE (available from Stratagene Cloning Systems, 11099 North Torrey Pines Road, La Jolla, Calif. 92037) the transformed culture is plated on ampicillin media plates and resistant colonies are selected. Plasmid DNA is isolated from transformants and examined by restriction analysis for the presence of the correct fragment. For expression of the recombinant NAF-1, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the NAF-1 HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells were lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with an HA specific monoclonal antibody. Proteins precipitated are analyzed on 15% SDS-PAGE gels.

Example 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ram's F12 media, with 10% FBS, penicillin and streptomycin, is added. This is then incubated at 37∞ C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeicr, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polypeptide comprising an amino acid sequence selected from the group consisting of:
   (a) amino acids 1 to 331 of SEQ ID NO:2;
   (b) the complete amino acid sequence encoded by the cDNA clone contained in ATCC Deposit No. 97343;
   (c) amino acids 2 to 331 of SEQ ID NO:2;
   (d) the complete amino acid sequence excepting the N-terminal methionine encoded by the cDNA clone contained in ATCC Deposit No. 97343;
   (e) amino acids 24 to 331 of SEQ ID NO:2;
   (f) amino acids 27 to 331 of SEQ ID NO:2; and
   (g) the amino acid sequence of the mature form of NAF-1 encoded by the cDNA clone contained in ATCC Deposit No. 97343.

2. The isolated polypeptide of claim 1 wherein said amino acid sequence is (a).

3. The isolated polypeptide of claim 1 wherein said amino acid sequence is (b).

4. The isolated polypeptide of claim 1 wherein said amino acid sequence is (c).

5. The isolated polypeptide of claim 1 wherein said amino acid sequence is (d).

6. The isolated polypeptide of claim 1 wherein said amino acid sequence is (e).

7. The isolated polypeptide of claim 1 wherein said amino acid sequence is (f).

8. The isolated polypeptide of claim 1 wherein said amino acid sequence is (g).

9. An epitope bearing fragment of the human NAF-1 polypeptide selected from the group consisting of:
   (a) an epitope bearing fragment consisting of at least amino acids 75 to 100 of SEQ ID NO:2;
   (b) an epitope bearing fragment consisting of at least amino acids 168 to 180 of SEQ ID NO:2;
   (c) an epitope bearing fragment consisting of at least amino acids 204 to 226 of SEQ ID NO:2;
   (d) an epitope bearing fragment consisting of at least amino acids 258 to 281 of SEQ ID NO:2; and,
   (e) an epitope bearing fragment consisting of at least amino acids 291 to 327 of SEQ ID NO:2.

10. The epitope bearing fragment of claim 9 wherein said fragment is (a).

11. The epitope bearing fragment of claim 9 wherein said fragment is (b).

12. The epitope bearing fragment of claim 9 wherein said fragment is (c).

13. The epitope bearing fragment of claim 9 wherein said fragment is (d).

14. The epitope bearing fragment of claim 9 wherein said fragment is (e).

* * * * *

SEQUENCE LISTING

<160> NUMBER OF SEQ ID NOS: 19

<210> SEQ ID NO 1
<211> LENGTH: 1105
<212> TYPE: DNA
<213> ORGANISM: homo sapiens
<220> FEATURE:
<221> NAME/KEY: CDS
<222> LOCATION: (19)..(1011)

<400> SEQUENCE: 1

```
cgctgctcct gccgggtg atg gaa aac ccc agc ccg gcc gcc gcc ctg ggc         51
                    Met Glu Asn Pro Ser Pro Ala Ala Ala Leu Gly
                     1               5                   10 aag gcc ctc tgc gct ctc ctc ctg gcc act ctc ggc gcc gcc ggc cag         99
Lys Ala Leu Cys Ala Leu Leu Leu Ala Thr Leu Gly Ala Ala Gly Gln
             15                  20                  25 cct ctt ggg gga gag tcc atc tgt tcc gcc aga gcc ctg gcc aaa tac        147
Pro Leu Gly Gly Glu Ser Ile Cys Ser Ala Arg Ala Leu Ala Lys Tyr
         30                  35                  40 agc atc acc ttc acg ggc aag tgg agc cag acg gcc ttc ccc aag cag        195
Ser Ile Thr Phe Thr Gly Lys Trp Ser Gln Thr Ala Phe Pro Lys Gln
     45                  50                  55 tac ccc ctg ttc cgc ccc cct gcc cag tgg tct tcg ctg ctg ggg gcc        243
Tyr Pro Leu Phe Arg Pro Pro Ala Gln Trp Ser Ser Leu Leu Gly Ala
 60                  65                  70                  75 gcg cat agc tcc gac tac agc atg tgg agg aag aac cag tac gtc agt        291
Ala His Ser Ser Asp Tyr Ser Met Trp Arg Lys Asn Gln Tyr Val Ser
                 80                  85                  90 aac ggg ctg cgc gac ttt gcg gag cgc ggc gag gcc tgg gcg ctg atg        339
Asn Gly Leu Arg Asp Phe Ala Glu Arg Gly Glu Ala Trp Ala Leu Met
             95                 100                 105 aag gag atc gag gcg gcg ggg gag gcg ctg cag agc gtg cac gcg gtg        387
Lys Glu Ile Glu Ala Ala Gly Glu Ala Leu Gln Ser Val His Ala Val
        110                 115                 120 ttt tcg gcg ccc gcc gtc ccc agc ggc acc ggg cag acg tcg gcg gag        435
Phe Ser Ala Pro Ala Val Pro Ser Gly Thr Gly Gln Thr Ser Ala Glu
    125                 130                 135 ctg gag gtg cag cgc agg cac tcg ctg gtc tcg ttt gtg gtg cgc atc        483
Leu Glu Val Gln Arg Arg His Ser Leu Val Ser Phe Val Val Arg Ile
140                 145                 150                 155 gtg ccc agc ccc gac tgg ttc gtg ggc gtg gac agc ctg gac ctg tgc        531
Val Pro Ser Pro Asp Trp Phe Val Gly Val Asp Ser Leu Asp Leu Cys
                160                 165                 170 gac ggg gac cgt tgg cgg gaa cag gcg gcg ctg gac ctg tac ccc tac        579
```

```
                                                                                              -continued Asp Gly Asp Arg Trp Arg Glu Gln Ala Ala Leu Asp Leu Tyr Pro Tyr
            175                 180                 185 gac gcc ggg acg gac agc ggc ttc acc ttc tcc tcc ccc aac ttc gcc       627
Asp Ala Gly Thr Asp Ser Gly Phe Thr Phe Ser Ser Pro Asn Phe Ala
        190                 195                 200 acc atc ccg cag gac acg gtg acc gag ata acg tcc tcc tct ccc agc       675
Thr Ile Pro Gln Asp Thr Val Thr Glu Ile Thr Ser Ser Ser Pro Ser
    205                 210                 215 cac ccg gcc aac tcc ttc tac tac ccg cgg ctg aag gcc ctg cct ccc       723
His Pro Ala Asn Ser Phe Tyr Tyr Pro Arg Leu Lys Ala Leu Pro Pro
220                 225                 230                 235 atc gcc agg gtg aca ctg gtg cgg ctg cga cag agc ccc agg gcc ttc       771
Ile Ala Arg Val Thr Leu Val Arg Leu Arg Gln Ser Pro Arg Ala Phe
                240                 245                 250 atc cct ccc gcc cca gtc ctg ccc agc agg gac aat gag att gta gac       819
Ile Pro Pro Ala Pro Val Leu Pro Ser Arg Asp Asn Glu Ile Val Asp
            255                 260                 265 agc gcc tca gtt cca gaa acg ccg ctg gac tgc gag gtc tcc ctg tgg       867
Ser Ala Ser Val Pro Glu Thr Pro Leu Asp Cys Glu Val Ser Leu Trp
        270                 275                 280 tcg tcc tgg gga ctg tgc gga ggc cac tgt ggg agg ctc ggg acc aag       915
Ser Ser Trp Gly Leu Cys Gly Gly His Cys Gly Arg Leu Gly Thr Lys
    285                 290                 295 agc agg act cgc tac gtc cgg gtc cag ccc gcc aac aac ggg agc ccc       963
Ser Arg Thr Arg Tyr Val Arg Val Gln Pro Ala Asn Asn Gly Ser Pro
300                 305                 310                 315 tgc ccc gag ctc gaa gaa gag gct gag tgc gtc cct gat aac tgc gtc      1011
Cys Pro Glu Leu Glu Glu Glu Ala Glu Cys Val Pro Asp Asn Cys Val
                320                 325                 330 taagaccaga gccccgcagc ccctggggcc cccggagcc atgggtgtc gggggctcct      1071 gtgcaggctc atgctgcagg cggccgaggg caca                                1105

<210> SEQ ID NO 2
<211> LENGTH: 331
<212> TYPE: PRT
<213> ORGANISM: homo sapiens

<400> SEQUENCE: 2

Met Glu Asn Pro Ser Pro Ala Ala Ala Leu Gly Lys Ala Leu Cys Ala
1               5                   10                  15

Leu Leu Leu Ala Thr Leu Gly Ala Ala Gly Gln Pro Leu Gly Gly Glu
            20                  25                  30

Ser Ile Cys Ser Ala Arg Ala Leu Ala Lys Tyr Ser Ile Thr Phe Thr
        35                  40                  45

Gly Lys Trp Ser Gln Thr Ala Phe Pro Lys Gln Tyr Pro Leu Phe Arg
    50                  55                  60

Pro Pro Ala Gln Trp Ser Ser Leu Leu Gly Ala Ala His Ser Ser Asp
65                  70                  75                  80

Tyr Ser Met Trp Arg Lys Asn Gln Tyr Val Ser Asn Gly Leu Arg Asp
                85                  90                  95

Phe Ala Glu Arg Gly Glu Ala Trp Leu Met Lys Glu Ile Glu Ala
            100                 105                 110

Ala Gly Glu Ala Leu Gln Ser Val His Ala Val Phe Ser Ala Pro Ala
        115                 120                 125

Val Pro Ser Gly Thr Gly Gln Thr Ser Ala Glu Leu Glu Val Gln Arg
    130                 135                 140

Arg His Ser Leu Val Ser Phe Val Val Arg Ile Val Pro Ser Pro Asp
```

-continued

```
145                 150                 155                 160
Trp Phe Val Gly Val Asp Ser Leu Asp Leu Cys Asp Gly Asp Arg Trp
                165                 170                 175

Arg Glu Gln Ala Ala Leu Asp Leu Tyr Pro Tyr Asp Ala Gly Thr Asp
            180                 185                 190

Ser Gly Phe Thr Phe Ser Ser Pro Asn Phe Ala Thr Ile Pro Gln Asp
        195                 200                 205

Thr Val Thr Glu Ile Thr Ser Ser Pro Ser His Pro Ala Asn Ser
    210                 215                 220

Phe Tyr Tyr Pro Arg Leu Lys Ala Leu Pro Pro Ile Ala Arg Val Thr
225                 230                 235                 240

Leu Val Arg Leu Arg Gln Ser Pro Arg Ala Phe Ile Pro Pro Ala Pro
                245                 250                 255

Val Leu Pro Ser Arg Asp Asn Glu Ile Val Asp Ser Ala Ser Val Pro
            260                 265                 270

Glu Thr Pro Leu Asp Cys Glu Val Ser Leu Trp Ser Ser Trp Gly Leu
        275                 280                 285

Cys Gly Gly His Cys Gly Arg Leu Gly Thr Lys Ser Arg Thr Arg Tyr
    290                 295                 300

Val Arg Val Gln Pro Ala Asn Asn Gly Ser Pro Cys Pro Glu Leu Glu
305                 310                 315                 320

Glu Glu Ala Glu Cys Val Pro Asp Asn Cys Val
                325                 330

<210> SEQ ID NO 3
<211> LENGTH: 36
<212> TYPE: DNA
<213> ORGANISM: oligonucleotide
<220> FEATURE:
<221> NAME/KEY: primer_bind
<222> LOCATION: (1)..(36)
<223> OTHER INFORMATION: 5' primer containing a BamHI restriction enzyme
      site followed by 21 nucleotides of NAD-1 coding sequence.

<400> SEQUENCE: 3
gccatacggg atccccagcc tcttggggga gagtcc                                36

<210> SEQ ID NO 4
<211> LENGTH: 35
<212> TYPE: DNA
<213> ORGANISM: oligonucleotide
<220> FEATURE:
<221> NAME/KEY: primer_bind
<222> LOCATION: (1)..(35)
<223> OTHER INFORMATION: 3' primer containing complementary sequence to
      an XbaI site followed by 21 nucleotides of NAF-1 sequence.

<400> SEQUENCE: 4
ggcatacgtc tagattagac gcagttatca gggac                                 35

<210> SEQ ID NO 5
<211> LENGTH: 41
<212> TYPE: DNA
<213> ORGANISM: oligonucleotide
<220> FEATURE:
<221> NAME/KEY: primer_bind
<222> LOCATION: (1)..(41)
<223> OTHER INFORMATION: 5' primer containing a BamHI restriction enzyme
      site followed by 8 nucleotides resembling an efficient signal for
      initiation of translation in eukaryotic cells followed by 21
      nucleotides of NAF-1 sequence.

<400> SEQUENCE: 5
```

-continued gccatacggg atccgccatc atggaaaacc ccagcccggc c               41

<210> SEQ ID NO 6
<211> LENGTH: 35
<212> TYPE: DNA
<213> ORGANISM: oligonucleotide
<220> FEATURE:
<221> NAME/KEY: primer_bind
<222> LOCATION: (1)..(35)
<223> OTHER INFORMATION: 3' primer containing the cleavage site for XbaI
      restriction endonuclease and 21 nucleotides complementary to the
      3' end of the translated sequence of the NAF-1 gene.

<400> SEQUENCE: 6
ggcatacgtc tagattagac gcagttatca gggac               35

<210> SEQ ID NO 7
<211> LENGTH: 392
<212> TYPE: PRT
<213> ORGANISM: rat

<400> SEQUENCE: 7

Pro Thr Gly Thr Gly Cys Val Ile Leu Lys Ala Ser Ile Val Gln Lys
1               5                   10                  15

Arg Ile Ile Tyr Phe Gln Asp Glu Gly Ser Leu Thr Lys Lys Leu Cys
            20                  25                  30

Glu Gln Asp Pro Thr Leu Asp Gly Val Thr Asp Arg Pro Ile Leu Asp
        35                  40                  45

Cys Cys Ala Cys Gly Thr Ala Lys Tyr Arg Leu Thr Phe Tyr Gly Asn
    50                  55                  60

Trp Ser Glu Lys Thr His Pro Lys Asp Tyr Pro Arg Ala Asn His
65                  70                  75                  80

Trp Ser Ala Ile Ile Gly Gly Ser His Ser Lys Asn Tyr Val Leu Trp
                85                  90                  95

Glu Tyr Gly Gly Tyr Ala Ser Glu Gly Val Lys Gln Val Ala Glu Leu
            100                 105                 110

Gly Ser Pro Val Lys Met Glu Glu Ile Arg Gln Gln Ser Asp Glu
        115                 120                 125

Val Leu Thr Val Ile Lys Ala Lys Ala Gln Trp Pro Ser Trp Gln Pro
130                 135                 140

Val Asn Val Arg Ala Ala Pro Ser Ala Glu Phe Ser Val Asp Arg Thr
145                 150                 155                 160

Arg His Leu Met Ser Phe Leu Thr Met Met Gly Pro Ser Pro Asp Trp
                165                 170                 175

Asn Val Gly Leu Ser Ala Glu Asp Leu Cys Thr Lys Glu Cys Gly Trp
            180                 185                 190

Val Gln Lys Val Val Gln Asp Leu Ile Pro Trp Asp Ala Gly Thr Asp
        195                 200                 205

Ser Gly Val Thr Tyr Glu Ser Pro Asn Lys Pro Thr Ile Pro Gln Glu
    210                 215                 220

Lys Ile Arg Pro Leu Thr Ser Leu Asp His Pro Gln Ser Pro Phe Tyr
225                 230                 235                 240

Asp Pro Glu Gly Gly Ser Ile Thr Gln Val Ala Arg Val Ile Glu
                245                 250                 255

Arg Ile Ala Arg Lys Gly Glu Gln Cys Asn Ile Val Pro Asp Asn Val
            260                 265                 270

Asp Asp Ile Val Ala Asp Leu Ala Pro Glu Glu Lys Asp Glu Asp Asp

```
                275              280              285
Thr Pro Glu Thr Cys Ile Tyr Ser Asn Trp Ser Pro Trp Ser Ala Cys
            290                  295                  300

Ser Ser Ser Thr Cys Glu Lys Gly Lys Arg Met Arg Gln Arg Met Leu
305                  310                  315                  320

Lys Ala Gln Leu Asp Leu Ser Val Pro Cys Pro Asp Thr Gln Asp Phe
                325                  330                  335

Gln Pro Cys Met Gly Pro Gly Cys Ser Asp Glu Asp Gly Ser Thr Cys
                340                  345                  350

Thr Met Ser Glu Trp Ile Thr Trp Ser Pro Cys Ser Val Ser Cys Gly
                355                  360                  365

Met Gly Met Arg Ser Arg Glu Arg Tyr Val Lys Gln Phe Pro Glu Asp
        370                  375                  380

Gly Ser Val Cys Met Leu Pro Thr
385                  390

<210> SEQ ID NO 8
<211> LENGTH: 52
<212> TYPE: PRT
<213> ORGANISM: rat

<400> SEQUENCE: 8

Cys Ile Tyr Ser Asn Trp Ser Pro Trp Ser Ala Cys Ser Ser Ser Thr
1               5                   10                  15

Cys Glu Lys Gly Lys Arg Met Arg Gln Arg Met Leu Lys Ala Gln Leu
            20                  25                  30

Asp Leu Ser Val Pro Cys Pro Asp Thr Gln Asp Phe Gln Pro Cys Met
        35                  40                  45

Gly Pro Gly Cys
    50

<210> SEQ ID NO 9
<211> LENGTH: 53
<212> TYPE: PRT
<213> ORGANISM: rat

<400> SEQUENCE: 9

Cys Thr Met Ser Glu Trp Ile Thr Trp Ser Pro Cys Ser Val Ser Cys
1               5                   10                  15

Gly Met Gly Met Arg Ser Arg Glu Arg Tyr Val Lys Gln Phe Pro Glu
            20                  25                  30

Asp Gly Ser Val Cys Met Leu Pro Thr Glu Thr Glu Lys Cys Thr
        35                  40                  45

Val Asn Glu Glu Cys
    50

<210> SEQ ID NO 10
<211> LENGTH: 52
<212> TYPE: PRT
<213> ORGANISM: rat

<400> SEQUENCE: 10

Cys Leu Val Thr Glu Trp Gly Glu Trp Asp Asp Cys Ser Ala Thr Cys
1               5                   10                  15

Gly Met Gly Met Lys Lys Arg His Arg Met Val Lys Met Ser Pro Ala
            20                  25                  30

Asp Gly Ser Met Cys Lys Ala Glu Thr Ser Gln Ala Glu Lys Cys Met
        35                  40                  45
```

```
Met Pro Glu Cys
    50

<210> SEQ ID NO 11
<211> LENGTH: 51
<212> TYPE: PRT
<213> ORGANISM: rat

<400> SEQUENCE: 11

Cys Leu Leu Ser Pro Trp Ser Glu Trp Ser Asp Cys Ser Val Thr Cys
1               5                   10                  15

Gly Lys Gly Met Arg Thr Arg Gln Arg Met Leu Lys Ser Leu Ala Glu
            20                  25                  30

Leu Gly Asp Cys Asn Glu Asp Leu Glu Gln Ala Glu Lys Cys Met Leu
        35                  40                  45

Pro Glu Cys
    50

<210> SEQ ID NO 12
<211> LENGTH: 52
<212> TYPE: PRT
<213> ORGANISM: rat

<400> SEQUENCE: 12

Cys Glu Leu Ser Glu Trp Ser Gln Trp Ser Glu Cys Asn Lys Ser Cys
1               5                   10                  15

Gly Lys Gly His Met Ile Arg Thr Arg Thr Ile Gln Met Glu Pro Gln
            20                  25                  30

Phe Gly Gly Ala Pro Cys Pro Glu Thr Val Gln Arg Lys Lys Cys Arg
        35                  40                  45

Ala Arg Lys Cys
    50

<210> SEQ ID NO 13
<211> LENGTH: 53
<212> TYPE: PRT
<213> ORGANISM: rat

<400> SEQUENCE: 13

Cys Arg Met Arg Pro Trp Thr Ala Trp Ser Glu Cys Thr Lys Leu Cys
1               5                   10                  15

Gly Gly Gly Ile Gln Glu Arg Tyr Met Thr Val Lys Lys Arg Phe Lys
            20                  25                  30

Ser Ser Gln Phe Thr Ser Cys Lys Asp Lys Lys Glu Ile Arg Ala Cys
        35                  40                  45

Asn Val His Pro Cys
    50

<210> SEQ ID NO 14
<211> LENGTH: 50
<212> TYPE: PRT
<213> ORGANISM: Homo sapiens

<400> SEQUENCE: 14

Cys Leu Val Ser Glu Trp Ser Glu Trp Ser Asp Cys Ser Thr Cys Gly
1               5                   10                  15

Lys Gly Met Arg Ser Arg Thr Arg Met Val Lys Met Ser Pro Ala Asp
            20                  25                  30

Gly Ser Pro Cys Pro Asp Thr Glu Glu Ala Glu Lys Cys Met Val Pro
```

-continued

```
                35                  40                  45

Glu Cys
    50

<210> SEQ ID NO 15
<211> LENGTH:
<212> TYPE:
<213> ORGANISM:

<400> SEQUENCE: 15

000

<210> SEQ ID NO 16
<211> LENGTH: 506
<212> TYPE: DNA
<213> ORGANISM: homo sapiens
<220> FEATURE:
<221> NAME/KEY: misc_feature
<222> LOCATION: (11)..(11)
<223> OTHER INFORMATION: n is equal to a, t, c, or g
<221> NAME/KEY: misc_feature
<222> LOCATION: (15)..(15)
<223> OTHER INFORMATION: n is equal to a, t, c, or g
<221> NAME/KEY: misc_feature
<222> LOCATION: (16)..(16)
<223> OTHER INFORMATION: n is equal to a, t, c, or g
<221> NAME/KEY: misc_feature
<222> LOCATION: (52)..(52)
<223> OTHER INFORMATION: n is equal to a, t, c, or g
<221> NAME/KEY: misc_feature
<222> LOCATION: (114)..(114)
<223> OTHER INFORMATION: n is equal to a, t, c, or g
<221> NAME/KEY: misc_feature
<222> LOCATION: (218)..(218)
<223> OTHER INFORMATION: n is equal to a, t, c, or g
<221> NAME/KEY: misc_feature
<222> LOCATION: (301)..(301)
<223> OTHER INFORMATION: n is equal to a, t, c, or g
<221> NAME/KEY: misc_feature
<222> LOCATION: (318)..(318)
<223> OTHER INFORMATION: n is equal to a, t, c, or g
<221> NAME/KEY: misc_feature
<222> LOCATION: (321)..(321)
<223> OTHER INFORMATION: n is equal to a, t, c, or g
<221> NAME/KEY: misc_feature
<222> LOCATION: (343)..(343)
<223> OTHER INFORMATION: n is equal to a, t, c, or g
<221> NAME/KEY: misc_feature
<222> LOCATION: (358)..(358)
<223> OTHER INFORMATION: n is equal to a, t, c, or g
<221> NAME/KEY: misc_feature
<222> LOCATION: (362)..(362)
<223> OTHER INFORMATION: n is equal to a, t, c, or g
<221> NAME/KEY: misc_feature
<222> LOCATION: (368)..(368)
<223> OTHER INFORMATION: n is equal to a, t, c, or g
<221> NAME/KEY: misc_feature
<222> LOCATION: (377)..(377)
<223> OTHER INFORMATION: n is equal to a, t, c, or g
<221> NAME/KEY: misc_feature
<222> LOCATION: (400)..(400)
<223> OTHER INFORMATION: n is equal to a, t, c, or g
<221> NAME/KEY: misc_feature
<222> LOCATION: (403)..(403)
<223> OTHER INFORMATION: n is equal to a, t, c, or g
<221> NAME/KEY: misc_feature
<222> LOCATION: (407)..(407)
<223> OTHER INFORMATION: n is equal to a, t, c, or g
<221> NAME/KEY: misc_feature
<222> LOCATION: (410)..(410)
<223> OTHER INFORMATION: n is equal to a, t, c, or g
<221> NAME/KEY: misc_feature
<222> LOCATION: (423)..(423)
<223> OTHER INFORMATION: n is equal to a, t, c, or g
<221> NAME/KEY: misc_feature
```

<222> LOCATION: (427)..(427)
<223> OTHER INFORMATION: n is equal to a, t, c, or g
<221> NAME/KEY: misc_feature
<222> LOCATION: (428)..(428)
<223> OTHER INFORMATION: n is equal to a, t, c, or g
<221> NAME/KEY: misc_feature
<222> LOCATION: (434)..(434)
<223> OTHER INFORMATION: n is equal to a, t, c, or g
<221> NAME/KEY: misc_feature
<222> LOCATION: (441)..(441)
<223> OTHER INFORMATION: n is equal to a, t, c, or g
<221> NAME/KEY: misc_feature
<222> LOCATION: (446)..(446)
<223> OTHER INFORMATION: n is equal to a, t, c, or g
<221> NAME/KEY: misc_feature
<222> LOCATION: (472)..(472)
<223> OTHER INFORMATION: n is equal to a, t, c, or g
<221> NAME/KEY: misc_feature
<222> LOCATION: (480)..(480)
<223> OTHER INFORMATION: n is equal to a, t, c, or g
<221> NAME/KEY: misc_feature
<222> LOCATION: (488)..(488)
<223> OTHER INFORMATION: n is equal to a, t, c, or g
<221> NAME/KEY: misc_feature
<222> LOCATION: (493)..(493)
<223> OTHER INFORMATION: n is equal to a, t, c, or g
<221> NAME/KEY: misc_feature
<222> LOCATION: (503)..(503)
<223> OTHER INFORMATION: n is equal to a, t, c, or g

<400> SEQUENCE: 16

```
gaattcggca naggnnaaac cccagcccgg ctgccgccct gggcaaggcc tnctgcgctc      60
tcctcctggc cactctcggc gccggcacca gcctcttggg ggagagtcca tctnttccgc    120
cagagccccg gccaaataca gcatcacctt cacgggcaag tggagccaga cggccttccc    180
caagcagtac cccctgttcc gccccccctgc gcatggtntt cgctgctggg ggccgcgcat   240
agctccgact acagcatgtg gaggaagaac cagtacgtca taaacgggct gcgcgacttt   300
ncggagcggc gaggcctngg ncgttgatga aggagatccg ggnggcgggg gaggcgtnca   360
anaggtgnca agagttnttt tcggggcccg gttccccaan ggnaacnggn aaacgttggg   420
ggntttnnag tttnaagaag naattnttgg ttttttttg ggtgggattt tnccaacccn    480
attgtttntg ggntggaaaa ttngac                                        506
```

<210> SEQ ID NO 17
<211> LENGTH: 316
<212> TYPE: DNA
<213> ORGANISM: homo sapiens
<220> FEATURE:
<221> NAME/KEY: misc_feature
<222> LOCATION: (5)..(5)
<223> OTHER INFORMATION: n is equal to a, t, c, or g
<221> NAME/KEY: misc_feature
<222> LOCATION: (6)..(6)
<223> OTHER INFORMATION: n is equal to a, t, c, or g
<221> NAME/KEY: misc_feature
<222> LOCATION: (43)..(3)
<223> OTHER INFORMATION: n is equal to a, t, c, or g
<221> NAME/KEY: misc_feature
<222> LOCATION: (129)..(129)
<223> OTHER INFORMATION: n is equal to a, t, c, or g
<221> NAME/KEY: misc_feature
<222> LOCATION: (130)..(130)
<223> OTHER INFORMATION: n is equal to a, t, c, or g
<221> NAME/KEY: misc_feature
<222> LOCATION: (138)..(138)
<223> OTHER INFORMATION: n is equal to a, t, c, or g
<221> NAME/KEY: misc_feature
<222> LOCATION: (143)..(143)
<223> OTHER INFORMATION: n is equal to a, t, c, or g
<221> NAME/KEY: misc_feature
<222> LOCATION: (164)..(164)

<223> OTHER INFORMATION: n is equal to a, t, c, or g
<221> NAME/KEY: misc_feature
<222> LOCATION: (258)..(258)
<223> OTHER INFORMATION: n is equal to a, t, c, or g
<221> NAME/KEY: misc_feature
<222> LOCATION: (272)..(272)
<223> OTHER INFORMATION: n is equal to a, t, c, or g
<221> NAME/KEY: misc_feature
<222> LOCATION: (276)..(276)
<223> OTHER INFORMATION: n is equal to a, t, c, or g
<221> NAME/KEY: misc_feature
<222> LOCATION: (278)..(278)
<223> OTHER INFORMATION: n is equal to a, t, c, or g
<221> NAME/KEY: misc_feature
<222> LOCATION: (287)..(287)
<223> OTHER INFORMATION: n is equal to a, t, c, or g
<221> NAME/KEY: misc_feature
<222> LOCATION: (301)..(301)
<223> OTHER INFORMATION: n is equal to a, t, c, or g
<221> NAME/KEY: misc_feature
<222> LOCATION: (312)..(312)
<223> OTHER INFORMATION: n is equal to a, t, c, or g

<400> SEQUENCE: 17

```
ggcanngcca gtacgtcata acgggctgcg cgactttgcg gangcggcga ggcctgggcg    60
ctgatgaagg agatcaaggc ggcgggggag gcgctgcaga ggtgcacgag gtgttttcgg   120
cgcccggtnn cccagcgnca ccnggcagac gtcggcgaac tggnaggtgc agcgcaggca   180
ctcgctggtc tcgtttgtgg tgcgcatcgt gcccagcccc gactggttcg tgggcgtgga   240
cagcctggga cctgtganaa cggggacctt tngcgngnaa caggcgncgt tggacctgta   300
nccctacgac gncggg                                                   316
```

<210> SEQ ID NO 18
<211> LENGTH: 316
<212> TYPE: DNA
<213> ORGANISM: homo sapiens
<220> FEATURE:
<221> NAME/KEY: misc_feature
<222> LOCATION: (5)..(5)
<223> OTHER INFORMATION: n is equal to a, t, c, or g
<221> NAME/KEY: misc_feature
<222> LOCATION: (6)..(6)
<223> OTHER INFORMATION: n is equal to a, t, c, or g
<221> NAME/KEY: misc_feature
<222> LOCATION: (43)..(43)
<223> OTHER INFORMATION: n is equal to a, t, c, or g
<221> NAME/KEY: misc_feature
<222> LOCATION: (129)..(129)
<223> OTHER INFORMATION: n is equal to a, t, c, or g
<221> NAME/KEY: misc_feature
<222> LOCATION: (130)..(130)
<223> OTHER INFORMATION: n is equal to a, t, c, or g
<221> NAME/KEY: misc_feature
<222> LOCATION: (138)..(138)
<223> OTHER INFORMATION: n is equal to a, t, c, or g
<221> NAME/KEY: misc_feature
<222> LOCATION: (143)..(143)
<223> OTHER INFORMATION: n is equal to a, t, c, or g
<221> NAME/KEY: misc_feature
<222> LOCATION: (164)..(164)
<223> OTHER INFORMATION: n is equal to a, t, c, or g
<221> NAME/KEY: misc_feature
<222> LOCATION: (258)..(258)
<223> OTHER INFORMATION: n is equal to a, t, c, or g
<221> NAME/KEY: misc_feature
<222> LOCATION: (272)..(272)
<223> OTHER INFORMATION: n is equal to a, t, c, or g
<221> NAME/KEY: misc_feature
<222> LOCATION: (276)..(276)
<223> OTHER INFORMATION: n is equal to a, t, c, or g
<221> NAME/KEY: misc_feature
<222> LOCATION: (278)..(278)
<223> OTHER INFORMATION: n is equal to a, t, c, or g -continued

```
<221> NAME/KEY: misc_feature
<222> LOCATION: (287)..(287)
<223> OTHER INFORMATION: n is equal to a, t, c, or g
<221> NAME/KEY: misc_feature
<222> LOCATION: (301)..(301)
<223> OTHER INFORMATION: n is equal to a, t, c, or g
<221> NAME/KEY: misc_feature
<222> LOCATION: (312)..(312)
<223> OTHER INFORMATION: n is equal to a, t, c, or g

<400> SEQUENCE: 18
ggcanngcca gtacgtcata acgggctgcg cgactttgcg gangcggcga ggcctgggcg      60
ctgatgaagg agatcaaggc ggcggggag gcgctgcaga ggtgcacgag gtgttttcgg     120
cgcccggtnn cccagcgnca ccnggcagac gtcggcgaac tggnaggtgc agcgcaggca    180
ctcgctggtc tcgtttgtgg tgcgcatcgt gcccagcccc gactggttcg tgggcgtgga    240
cagcctggga cctgtganaa cggggaccttt tngcgngnaa caggcgncgt tggacctgta   300
nccctacgac gncggg                                                   316

<210> SEQ ID NO 19
<211> LENGTH: 53
<212> TYPE: PRT
<213> ORGANISM: homo sapiens

<400> SEQUENCE: 19

Cys Glu Val Ser Leu Trp Ser Ser Trp Gly Leu Cys Gly Gly His Cys
1               5                   10                  15

Gly Arg Leu Gly Thr Lys Ser Arg Thr Arg Tyr Val Arg Val Gln Pro
            20                  25                  30

Ala Asn Asn Gly Ser Pro Cys Pro Glu Leu Glu Glu Glu Ala Glu Cys
        35                  40                  45

Val Pro Asp Asn Cys
    50
```